US00PP13602P2

(12) United States Plant Patent
Boeder

(10) Patent No.: US PP13,602 P2
(45) Date of Patent: Feb. 25, 2003

(54) CHRYSANTHEMUM PLANT NAMED 'FESTIVAL TIME IMPROVED'

(75) Inventor: Mark Roland Boeder, Den Haag (NL)

(73) Assignee: Cleangro Limited (GB)

( * ) Notice: Subject to any disclaimer, the term of this patent is extended or adjusted under 35 U.S.C. 154(b) by 0 days.

(21) Appl. No.: 09/957,494

(22) Filed: Sep. 19, 2001

(51) Int. Cl.[7] ..... A01H 5/00
(52) U.S. Cl. ..... Plt./291
(58) Field of Search ..... Plt./291, 297, 292

(56) References Cited

U.S. PATENT DOCUMENTS

PP9,843 P 4/1997 Van Koeveringe ..... Plt./287

*Primary Examiner*—Bruce R. Campell
*Assistant Examiner*—Michelle Kizilkaya
(74) *Attorney, Agent, or Firm*—Howrey Simon Arnold & White, LLP

(57) ABSTRACT

A new variety of Chrysanthemum plant named 'Festival Time Improved', having an upright free branching habit with medium vigour and slightly domed reflexing pink/dark pink bi-coloured flowers.

1 Drawing Sheet

LATIN NAME OF THE GENUS AND SPECIES

Botanical classification: *Dendranthema grandiflora.*

VARIETY DENOMINATION

The new Chrysanthemum variety denomination is 'Festival Time Improved'.

BACKGROUND OF THE INVENTION

The present invention comprises a new and distinct cultivar of Chrysanthemum botanically known as *Dendranthema grandiflora*, and referred to by the cultivar name 'Festival Time Improved'.

'Festival Time Improved', identified as 20278-9 was discovered as a natural mutation on a whole plant in a controlled cultivated planting of the variety 'Festival Time'. The new variety 'Festival Time Improved' has been asexually reproduced by vegetative cuttings at Chichester, West Sussex, United Kingdom and the distinguishing characteristics are retained through successive generations of asexual reproduction.

BRIEF SUMMARY OF THE INVENTION

'Festival Time Improved' is a pot type of Chrysanthemum plant variety having pale pink to purple decorative flowers with slightly reflexing form, giving a slightly domed capitulum.

Comparison with Parent

Plants of the new Chrysanthemum variety 'Festival Time Improved' are similar to the parent cultivar 'Festival Time' in plant habitat and growth rate. In side-by-side comparisons in Chichester, West Sussex, United Kingdom, under commercial practice, plants of the new Chrysanthemum variety 'Festival Time Improved' differed from plants of the parent cultivar 'Festival Time' in the following characteristics.

1. The new variety 'Festival Time Improved' produces pale pink to purple decorative color flowers whereas the parent cultivar 'Festival Time' produces pale pink to lighter purple decorative color flowers.

2. Plants of the new variety 'Festival Time Improved' have similar inflorescence plants as that of the parent cultivar 'Festival Time'.
3. 'Festival Time Improved' has flowers that are of a more uniform habit than 'Festival Time'.
4. 'Festival Time Improved' has flowers that are of a more defined color contrast than 'Festival Time'.

Comparison with Other Varieties

Plants of the new Chrysanthemum variety 'Festival Time Improved' are dissimilar to the cultivar 'Spring Delano' in plant habitat and growth rate. However, in side-by-side comparisons in Chichester, West Sussex, United Kingdom, under commercial practice, plants of the new Chrysanthemum variety 'Festival Time Improved' compared to plants of the cultivar 'Spring Delano' in the following characteristics.

1. The new variety 'Festival Time Improved' produces better color flowers, whereas the cultivar 'Spring Delano' produces weaker color flowers.
2. Plants of the new variety 'Festival Time Improved' have smaller and shorter inflorescence than plants of the cultivar 'Spring Delano'.
3. The new variety 'Festival Time Improved' has a better branching habit with more flowers, compared to the variety 'Spring Delano'.

BRIEF DESCRIPTION OF ILLUSTRATIONS

Typical specimens of the plant and flowers for the new Chrysanthemum variety 'Festival Time Improved' are shown in the accompanying photograph. The colors shown are as true as possible within the usual limits of this kind of illustration. FIG. 1 is a whole plant view of the new 'Festival Time Improved' grown in a pot. The plant shown in the illustration is 60 days from start of Short Days.

DETAILED BOTANICAL DESCRIPTION

The following description of the new Chrysanthemum variety 'Festival Time Improved' is of plants grown in a greenhouse in Chichesterr, West Sussex, United Kingdom in the month of August. The cultivar has not been observed under all possible environmental conditions. The phentoype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 18° C. at night and about 24° C. to 25° C. during the day under light conditions of about 5,000 to 6,000 foot candles. The plants respond well to the use of growth retardant, such as two B9 treatments at about 2000 ppm. To produce a commercial product the plants may be pinched once with the centre bud removed. The typical container size for commercial growth is 14 cm. It has been observed that the shelf life of the new variety is about 22 days with a response time of about 8 weeks. The new variety is suitable for growth in a temperature range of 16° C. to 25° C.

The new variety may be produced as a spray or disbud. The following description is with respect to a plant produced as Spray pot Chrysanthemums. In the description of this new Chrysanthemum variety, color values have been taken from The Royal Horticultural Society Colour Chart (R.H.S.C.C.).

Plant

Plant type: Pot.
Habit: Upright and branching.
Height: Medium 18 to 20 cm.
Width: Near 27 cm.
Branching characteristics: Upright and spreading.
Length of lateral branches: 10 to 15 cm.
Number of breaks from pinch: 4 to 6.
Stem colour: 147B.
Response time: 54 days.
Vigour: Medium.
Shelf life: Near 22 days.
Disease: No observations
Pest: No Observations
Growth retardant type and treatment: B9 85% 2 applications of 2 gram/litre at 2 days, 21 days after propagating unrooted vegetative cuttings.

The plants were grown for two weeks in Long Day conditions (20 hours of light) and then transferred to Short Day conditions (13 hours of dark).

Propagation:
*Type.*—Vegetative propagation via stem cuttings.
*Time to rooting.*—12–14 days with soil temperatures of 18° C.
*Rooting habit.*—Fine and fibrous.

Foliage

Number of leaves per Lateral Branch: 8 to 11.
Compound or single: Single.
Arrangement of Leaves: Alternate.
*Shape of leaf.*—Typically 5 lobed, ovate.
*Size of leaf.*—Width (cm): Near 4 cm. Length (cm): Near 7 cm.
*Leaf apex.*—Acute/Rounded.
*Base.*—Obtuse.
*Attachment.*—Petioled.
*Aspect.*—Slightly undulating.
*Margin.*—Palmately lobed.
*Surface characteristics.*—Top: Pubescent. Bottom: Pubescent.
Petiole:
*Colour.*—Near 137 B.
*Length.*—0.8 to 1 cm.
Venation: Net, prominent midvein and lateral veins at under side.
Colour:
*Upper side.*—Near 147 B.
*Under side.*—Near 147 B.
Colour:
*Mature leaf.*—Upper side: Near 137 A; Under side: Near 137 C.
*Young leaf.*—Upper side: Near 137 A; Under side: Near 137 C.

Flower

Flower Appearance: Slightly domed and reflexing. Circular.
Flower type: Decorative.
Flower Form: Slightly domed.
Flower shape: Circular.
Flower Habit: Upright.
Number of blossoms per branch: 3 to 5.
Inflorescence form: Cyme.
*Depth of fully expanded blossoms.*—Near 2½ cm.
*Diameter of fully expanded blossoms.*—Near 7 cm.
Phyllaries:
*Number.*—21 to 30.
*Colour.*—Near 137 A.
*Length.*—0.6 to 1.1 cm.
*Width.*—Near 0.3 cm.
*Texture/appearance.*—Pubescent.
Peduncles: Peduncle length is shortest at the terminal flower and progressively longer moving down the stem; longest length is on average 10 cm; shortest length on average 5 cm.
*Length.*—6 cm.
*Colour.*—Near 137 B.
*Surface.*—Pubescent.
*Habit.*—Slightly curving.
*Strength.*—Medium.
Pedicel:
*Length.*—Terminal: Near 4 cm; Lateral: Near 6 cm.
*Colour.*—Near 137 B.
*Surface.*—Pubescent.
*Habit.*—Slightly curving.
*Strength.*—Medium.
Ray florets:
*Form/shape.*—Reflexing.
*Texture/appearance.*—Shiny.
*Number per flower.*—200 to 220.
*Length.*—1.2 to 2.7 cm.
*Width.*—0.4 to 0.8 cm.
*Apex.*—Slightly dentate.
*Base.*—Tapered.
*Margin.*—Entire.
Disc florets: No known Disc Florets.
Fragrance: Slight.
Flower bud (at onset of color):
*Length.*—Near 0.9 cm.
*Diameter.*—Near 1.0 cm.
*Form/shape.*—Globular.
General flower color: Pale pink with dark pink center to flower.
*1. Ray florets, upper side.*—Immature: Near 67 B Mature: Paler than 36 D Older/Fading: Near 157 D 2. *Ray florets, under side.*—Immature: Near 67 B Mature: Paler than 36 D Older/Fading: Near 157 D.
3. *Disc florets.*—N/A.
4. *Bud.*—Near 138 A.

Flower progression: Flowers reflex and fade slightly with age, but color differential is maintained well into pot life.

Reproductive Organs

Gynoecium: Present on Ray florets.
*Pistil number.*—100+.
*Stigma color.*—Near 6 C.
*Stigma shape.*—*Forked.*
*Style color.*—Near 6 C.
*Style length.*—Near 0.5 cm.

Disc florets: Have not been observed.
Seed production: Has not been observed.

What is claimed is:

1. A new and distinct variety of Chrysanthemum plant, substantially as described and illustrated herein.

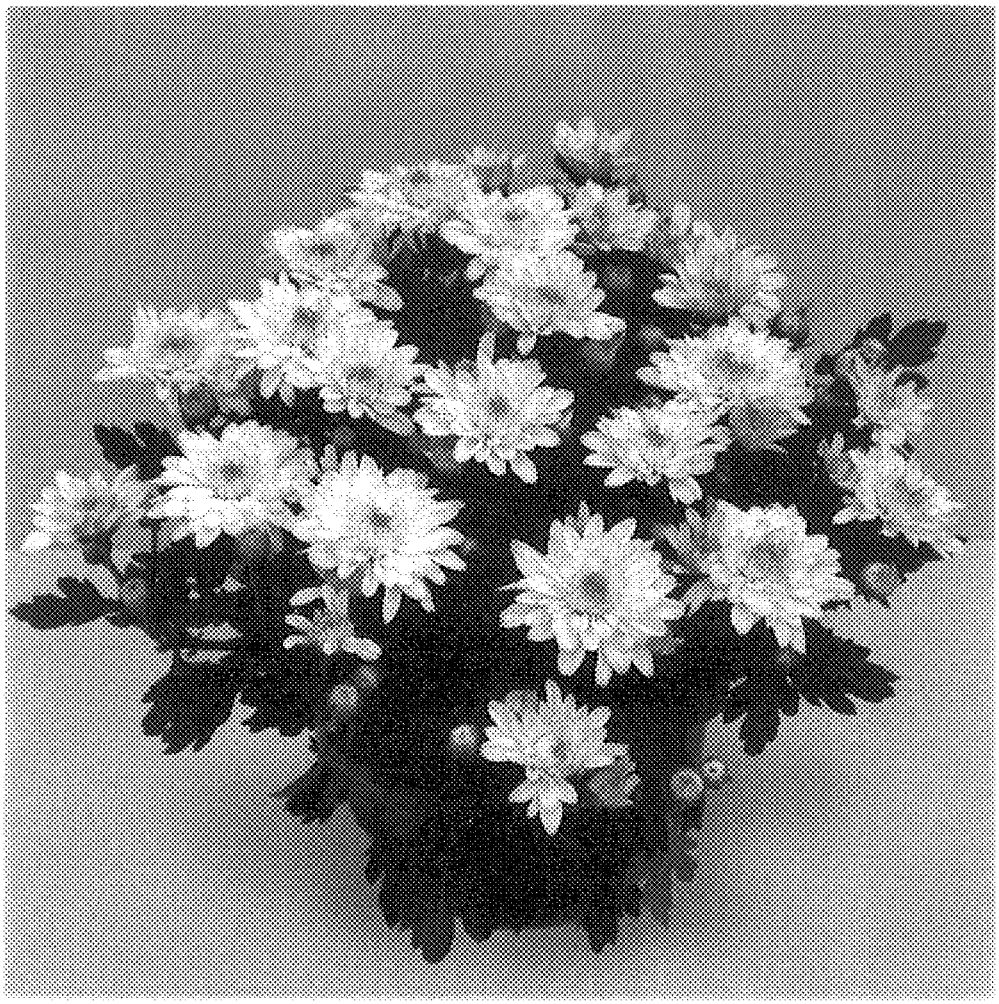

* * * * *